United States Patent [19]

Loescher et al.

[11] Patent Number: 5,005,568

[45] Date of Patent: Apr. 9, 1991

[54] ISOLATION VALVE

[75] Inventors: Thomas C. Loescher, Encinitas; Thomas P. Shanks, Temecula; Henry E. Garcia, Homeland, all of Calif.

[73] Assignee: Hudson Respiratory Care Inc., Temecula, Calif.

[21] Appl. No.: 320,868

[22] Filed: Mar. 7, 1989

Related U.S. Application Data

[63] Continuation of Ser. No. 105,726, Oct. 7, 1987, abandoned.

[51] Int. Cl.$^5$ .............................................. A61M 16/00
[52] U.S. Cl. .............................. 128/202.28; 128/203.11
[58] Field of Search ...................... 128/203.11, 202.29, 128/202.28, 205.24, 206.17

[56] References Cited

U.S. PATENT DOCUMENTS

| | | |
|---|---|---|
| 2,280,050 | 4/1942 | Alexander et al. ............ 128/203.11 |
| 3,018,775 | 1/1962 | Wilson et al. ................. 128/203.11 |
| 3,208,449 | 5/1964 | Bartlett, Jr. ................... 128/203.11 |
| 3,782,083 | 1/1974 | Rosenberg ........................... 55/491 |
| 3,932,153 | 1/1976 | Byrns ................................... 55/511 |
| 4,592,350 | 6/1986 | Maryyanek et al. ........... 128/206.17 |
| 4,622,964 | 11/1986 | Flynn ............................. 128/205.24 |

Primary Examiner—Lee S. Cohen
Assistant Examiner—J. P. Lacyk
Attorney, Agent, or Firm—Jerry R. Seiler

[57] ABSTRACT

An isolation valve for use in administering mouth-to-mouth emergency artificial respiration includes a housing having a fixed inlet pipe and a rotatable outlet pipe, a bacteria filter permanently secured in the housing member around the periphery of the filter whereby all of the gas passing through the device must pass through the filter, and a one-way valve seated in the housing and cooperating with valve seats for opening and closing exhaust ports.

7 Claims, 2 Drawing Sheets

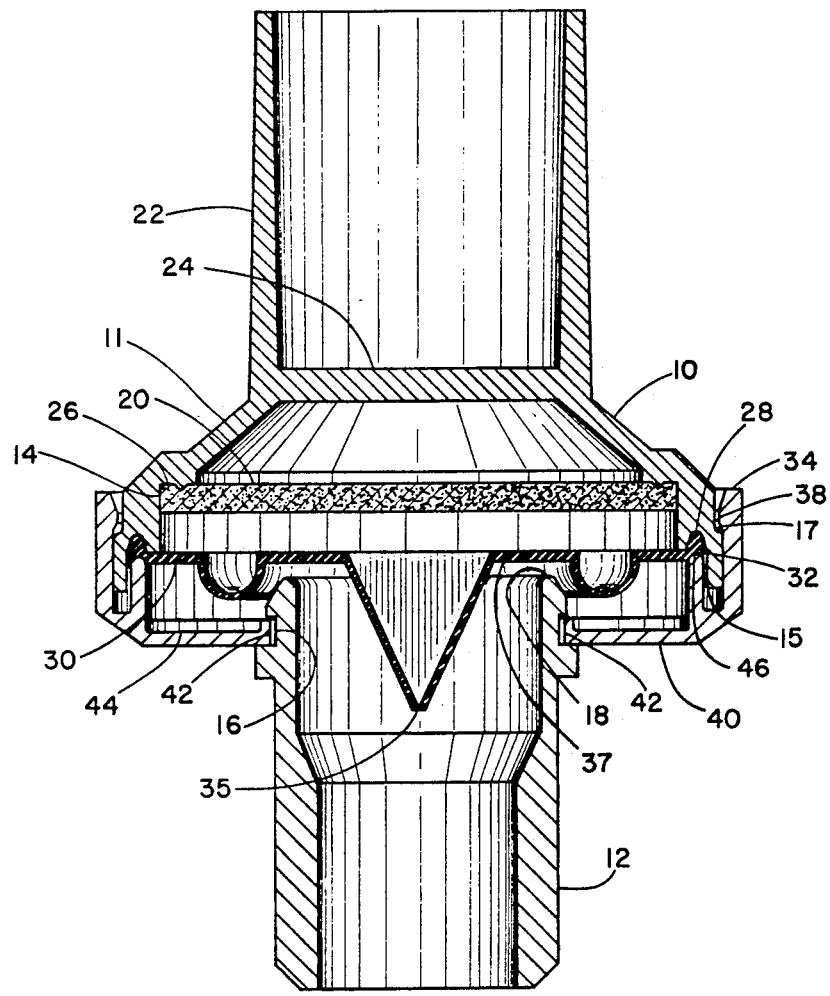
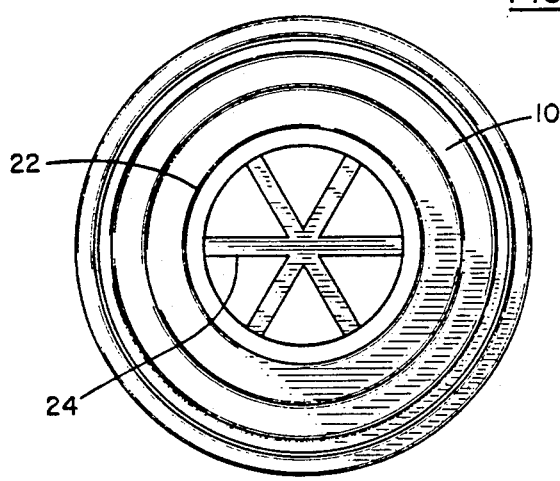
FIG. 2
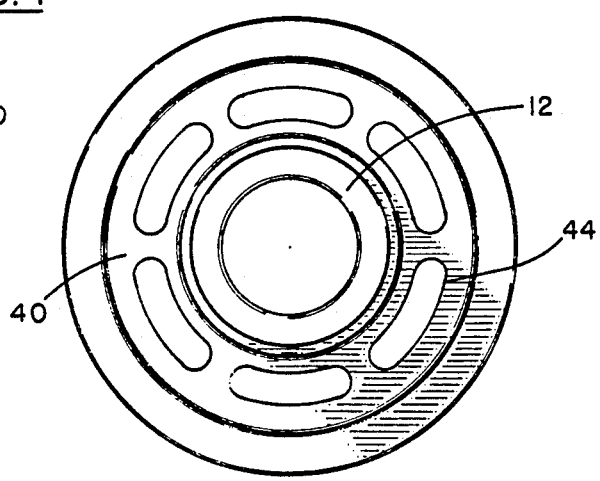
FIG. 3

ISOLATION VALVE

This is a continuation of co-pending application Ser. No. 07/105,726, filed on Oct. 7, 1987 now abandoned.

BACKGROUND OF THE INVENTION

One-way valves for administering emergency resuscitation are well known in the art. Such devices are used in combination with a mouthpiece for the rescuer to breathe into the device and a mask for being placed over the nose and mouth of the victim. The valves usually incorporate a disc-type one-way valve in which the disc moves between open or unseated and closed or seated positions, often guided by a post or similar means for guiding the moving disc. Such valves are disadvantageous in that the moving disc can sometimes become dislodged, or the presence of contaminating materials or vomitus may prevent the disc from seating or freely moving between open and closed positions. Moreover, most resuscitation valves do not use filters thereby potentially exposing either the rescuer or victim to cross-contamination of communicable diseases during use. Other such valves require the patient or victim to exhale against or through the valve and/or a filter when breathing is resumed.

SUMMARY OF THE INVENTION

The emergency resuscitation valve of the present invention includes substantially improved features including a fully-sealed filter secured entirely around its periphery to prevent dislodging, leaking or contamination, as well as a protection grill for the filter. The device also incorporates a one-way duckbill diaphragm to obviate the disadvantages of a moving disc-type valve. These as well as other advantages and features of the device will be described in the following detailed description.

BRIEF DESCRIPTION OF THE DRAWINGS

FIG. 1 is a side sectional view of the valve showing the components thereof;

FIG. 2 is an end view of the inlet end of the valve showing a filter protection grill;

FIG. 3 is an end view of the opposite outlet end showing a swivel pipe and exhalation ports.

DETAILED DESCRIPTION OF THE INVENTION

Figure 4:
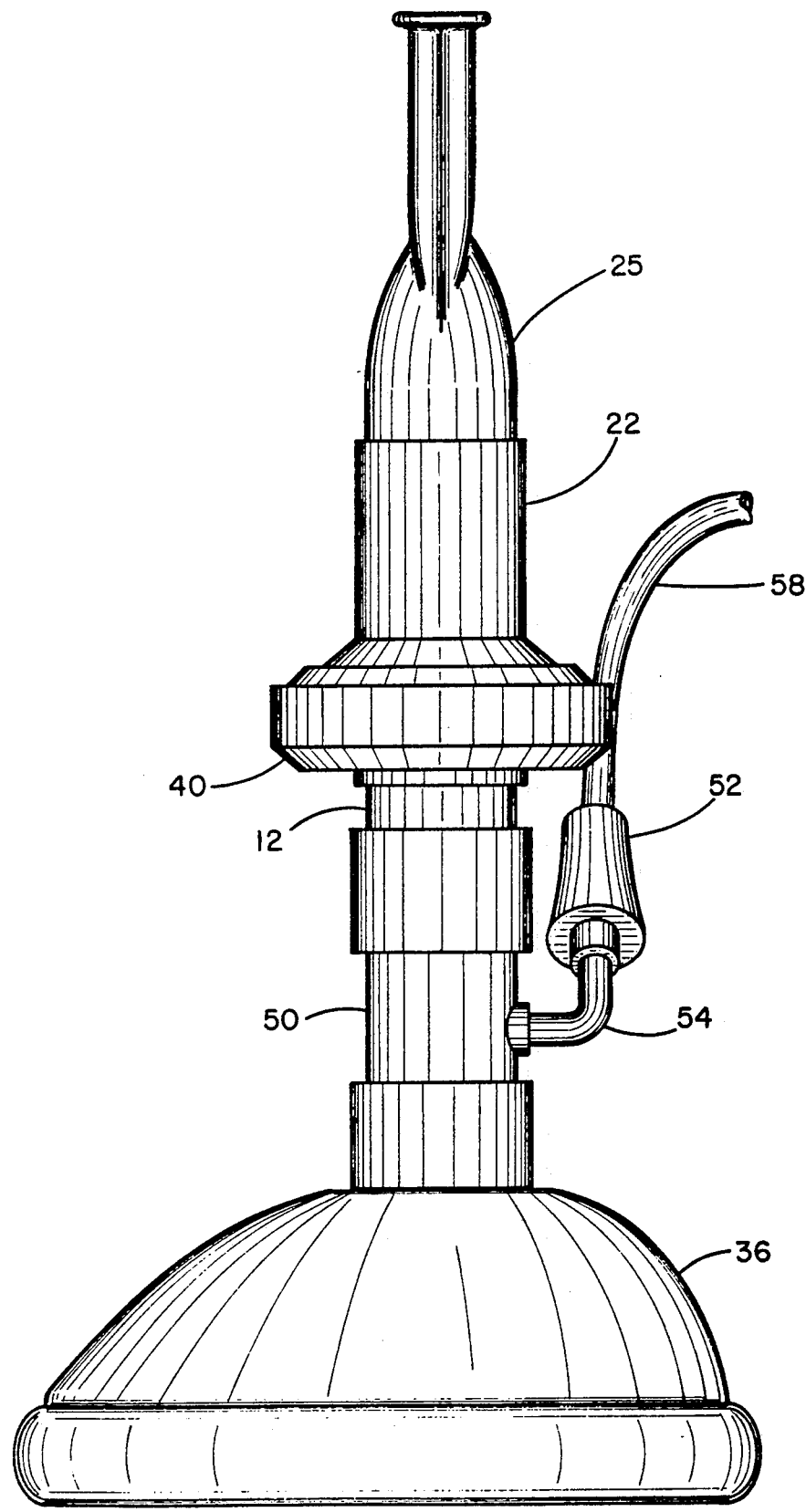
FIG. 4 is a side view of the valve connected to a mouthpiece, an oxygen-enrichment adapter and a mask.

Referring to FIG. 1, the isolation valve assembly is shown in section, the housing assembly comprising an inlet member portion 10 and a cap portion 40, these two components being secured together. Inlet member 10 is a unitary piece comprised of an inlet pipe 22, and wall portion 11 extending and flared circumferentially from the pipe to annular rim 15. Between pipe 22 and annular rim 15, the wall portion includes a shelf 26 for securing filter 20 and annular trough 28 for receiving the edge of diaphragm 30.

Cap portion 40 of the housing assembly includes an outer collar 34 having an enlarged lip 38 on the interior surface for engaging notch 17 formed along the exterior surface of inlet member 10 near the the end of annular lip 15. The dimensions of the two housing assembly components are such that cap 40 can be snap-fit on inlet member 10 during assembly by forcing collar 34 over annular lip 15 until lip 38 is seated into notch 17. Other means of securing these components such as tabs, bonding, welding, a threaded fitting or the like may also be used for joining the two housing assembly components.

A circular port 42 on cap 40, coaxial with inlet pipe 22, secures rotatable swivel pipe 12. Pipe 12 incorporates annular channel 16 having a diameter slightly smaller than the diameter of port 42 so that the pipe can be readily rotated relative to the rest of the valve assembly. This feature is most useful in allowing the rescuer to position himself comfortably at any angle relative to the patient when administering resuscitation.

Interiorly of the housing assembly is located filter 20 which is secured entirely around its peripheral edge 14 on shelf 26. The filter may be glued or otherwise sealed on the shelf. Because the filter is secured completely (fully sealed) across inlet member 10, gas passing through the valve via inlet pipe 22 must pass through the filter. Moreover, such a fully sealed filter will prevent it from being dislodged, leaking and prevent cross-contamination between the user and patient. The filter material and density are of substantial importance. The requirements are two-fold: the filter must be effective in substantially preventing passage of undesirable contaminants, especially those which transfer communicable diseases, and the filter material must not substantially reduce or restrict the flow of gas through the valve. Specifically, it is important that the back pressure or pressure resistance of a suitable resuscitation valve should be less than about 6 and preferably less than 5 centimeters of water at a flow of 50 liters per minute. A test for measuring such a flow resistance is covered in ASTM ISO/DIS 8382. Resuscitation valves having a greater flow resistance simply create excessive back pressure in excess of that which allows a rescuer to comfortably and effectively use the valve for emergency mouth-to-mouth resuscitation. For this purpose and to meet these critical requirements, applicants have found that "Filtrete" brand, type G synthetic air filter material available from 3M of St. Paul, Minn. is a useful filter material. Such a preferred filter material comprises a nonconductive polypropylene web of a density between $\frac{1}{2}$ and 1 oz/yd$^2$ of approximately $\frac{1}{4}$" thickness and imbedded with electrical charges. The fibers of the material are permanently charged electrets in which the positive and negative charges are physically embedded into the fiber surface creating electrostatic charges acting as magnets for attracting and filtering undesirable contaminants. As shown in FIG. 1, the relative dimensions of the exposed filter member surface and the diameter of the inlet pipe are such that the ratio of the inside diameter of the inlet pipe 24 to the diameter of the filter member surface exposed to the inlet pipe are about 1:1.5, respectively.

Diaphragm 30 is secured in the device between the filter and the outlet pipe. The diaphragm includes an outer annular lip 32 which is seated in annular trough 28 formed in inlet member 10. Annular rib 46 formed interiorly of cap 40 is forced against the upper surface of the diaphragm above diaphragm lip 32 thereby maintaining pressure forcing the diaphragm lip into trough 28 when the components are fully assembled as previously described and shown in FIG. 1. Thus, there is a gas-tight seal formed between diaphragm lip 32 and trough 28 whereby all of the gas passing from inlet pipe 22 to outlet pipe 12 must pass through duckbill valve port 35. The flexible duckbill diaphragm forms a one-way valve with port 35 closed in the rest position shown where pressure is substantially equalized between the inlet and outlet sides of the valve. Port 35 opens and allows gas to pass from the inlet pipe to outlet pipe 12 when a rescuer forces air into the inlet pipe. When pressure on the outlet side of the diaphragm is greater, port 35 is again closed to prevent gas from passing. Cap 40 is provided with one or more enlarged exhaust ports 44 as shown in FIG. 2 which dump or vent gas exhaled into outlet pipe 12 by the patient or victim when breathing is resumed. Thus, the exhaled patient gas is vented to atmosphere, practically without restriction or back pressure and without passing through a valve or filter.

A further advantage of the device of the invention incorporates means for protecting the filter from damage or the like from outside of the device. Such means comprises grill 24, as also shown in FIG. 2, having ribs extending across the opening between inlet pipe 22 and the interior of inlet member 10. The presence of the grill prevents substantial access to and exposure of the filter from objects or a user's fingers inserted into the inlet pipe which could otherwise disturb or damage the filter. The grill shown also is preferably integrally formed with the inlet member thus obviating the need of separate assembly as well as its misalignment during assembly or later being displaced. The specific form or shape of the grill or its components is not so important, so long as it does not substantially affect or inhibit the flow of gas through or into the device.

In FIG. 4 the valve of the invention is illustrated together with an oxygen enrichment adapter 50, an optional device which is used when supplemental oxygen is required or desired in resuscitating a patient. Such an adapter includes elbow 54, adapter pipe 52, and to which is attached oxygen supply tubing 58. Mouthpiece 25 is inserted in inlet pipe 22 and oxygen enrichment adapter 50 is secured to outlet pipe 12. A mask 36 for being placed on the face of a victim or patient is attached to the other end of adapter 50. In the event supplemental oxygen is not desired, oxygen enrichment adapter 50 is unnecessary and mask 36 is attached directly to outlet pipe 12.

Referring again to FIGS. 1 and 4, during use, the rescuer will place mask 36 on the face of a victim or patient who is usually lying face up. The rescuer places his or her mouth on mouthpiece 25 and exhales thereby forcing air through inlet pipe 22, past filter 20 out through duckbill port 35, through outlet pipe 12, into mask 36 and into the patient's or victim's airway. During this time, flexible diaphragm 30 is also urged from the rest position shown in FIG. 1 toward outlet pipe 12 whereby diaphragm surface 37 contacts valve seat 18 at the interior end of outlet pipe 12 forming a gas-tight seal. Thus, substantially all of the gas forced into the device by the rescuer passes through duckbill port 35 which remains open as long as the rescuer exhales into the device. Once the rescuer terminates exhalation into the valve, diaphragm 30 returns to its normal rest position shown in FIG. 1 with port 35 closed. When the victim exhales into mask 36 air forced into pipe 12 will pass between diaphragm surface 37, valve seat 18 and out through exhalation ports 44. Moreover, with duckbill port 35 is closed, no gas enters into the valve beyond the diaphragm. These as well as other advantages and uses of the device within the purview of the invention will be evident to one skilled in the art.

I claim:

1. An isolation valve assembly for use in administering mouth-to-mouth emergency artificial respiration comprising:

a housing assembly comprising an inlet member having a first cylindrical wall portion and an inlet pipe extending therefrom having an inside first diameter, and an outlet member having a second cylindrical wall portion with a plurality of exhaust ports therethrough and an outlet pipe extending therefrom having an inside second diameter, said first and second cylindrical wall portions being matingly engaged to define an interior chamber having a third diameter, which is greater than either said first or said second diameter, a flexible diaphragm secured across said interior chamber, said diaphragm having a one-way valve therein for allowing gas to pass only from said inlet member to said outlet member and sealing means for forming a gas tight seal against said outlet member and closing said exhaust ports when gas is directed through said one-way valve, and a cylindrical filter member spaced apart from said inlet pipe and secured in and extending across said interior chamber between said inlet pipe and said diaphragm, said filter member having a diameter greater than the inside diameter of either said inlet pipe or said outlet pipe, wherein said valve assembly has a back pressure of less than about 6 cm $H_2O$ at a flow of 50 liters per minute.

2. The valve assembly of claim 1 wherein said filter member is secured to said first cylindrical wall portion.

3. The valve assembly of claim 2 including a grill member in said inlet pipe for protecting said filter member.

4. The valve assembly of claim 3 wherein said first cylindrical wall portion includes a shelf extending therearound and wherein said cylindrical filter member includes a peripheral edge secured on said shelf.

5. The valve assembly of claim 1 wherein said valve is a duckbill valve.

6. The valve assembly of claim 1 including a mouthpiece secured to said inlet pipe and a face mask secured to said outlet pipe.

7. The valve assembly of claim 1 wherein the ratio of the inside diameter of said inlet pipe: diameter of said filter member surface exposed to said inlet pipe is about 1:1.5, respectively.

* * * * *